(12) United States Patent
Johnson et al.

(10) Patent No.: US 12,144,730 B2
(45) Date of Patent: Nov. 19, 2024

(54) HEART VALVES WITH INCREASED EFFECTIVE ORIFICE AREA

(71) Applicant: Edwards Lifesciences Corporation, Irvine, CA (US)

(72) Inventors: Derrick Johnson, Orange, CA (US); Van Huynh, Anaheim, CA (US); Qinggang Zeng, Mission Viejo, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 123 days.

(21) Appl. No.: 17/653,843

(22) Filed: Mar. 7, 2022

(65) Prior Publication Data

US 2022/0183832 A1    Jun. 16, 2022

Related U.S. Application Data

(60) Continuation of application No. 15/591,915, filed on May 10, 2017, now Pat. No. 11,266,499, which is a (Continued)

(51) Int. Cl.
  *A61F 2/24* (2006.01)
(52) U.S. Cl.
  CPC .......... *A61F 2/2418* (2013.01); *A61F 2/2409* (2013.01); *A61F 2/2412* (2013.01);
  (Continued)
(58) Field of Classification Search
  None
  See application file for complete search history.

(56) References Cited

U.S. PATENT DOCUMENTS

| 30,912 A | 12/1860 | Hancock |
| 3,143,742 A | 8/1964 | Cromie |

(Continued)

FOREIGN PATENT DOCUMENTS

| EP | 0116236 A1 | 8/1984 |
| EP | 0125393 A1 | 11/1984 |

(Continued)

OTHER PUBLICATIONS

International Search Report from corresponding PCT case No. PCT/US2014/056070 dated Dec. 24, 2014.

*Primary Examiner* — Ann Schillinger
(74) *Attorney, Agent, or Firm* — Guy Cumberbatch (57) ABSTRACT

A prosthetic heart valve for implant in a human. The valve includes a wireform with undulating inflow cusps and outflow commissure posts to which flexible leaflets attach and coapt in a flow area. Each leaflet may drape over the top of the wireform in the cusp area, but have tabs that each extend underneath the wireform at the commissure posts to be secured along with a tab of an adjacent leaflet. The prosthetic heart valve may also be a dual-wire wireform, with the leaflets sandwiched therebetween. One wireform may be larger than the other, with the leaflets extending over the smaller wireform. The smaller wireform may have commissures that bend radially outward from the larger wireform to provide structure to which the leaflet tabs attach.

21 Claims, 8 Drawing Sheets

Related U.S. Application Data division of application No. 14/488,728, filed on Sep. 17, 2014, now Pat. No. 10,441,415.

(60) Provisional application No. 61/880,688, filed on Sep. 20, 2013.

(52) U.S. Cl.
CPC ..... *A61F 2210/00* (2013.01); *A61F 2250/006* (2013.01); *A61F 2310/00389* (2013.01)

(56) References Cited

U.S. PATENT DOCUMENTS

| | | | |
|---|---|---|---|
| 3,320,972 | A | 5/1967 | High et al. |
| 3,371,352 | A | 3/1968 | Siposs et al. |
| 3,546,710 | A | 12/1970 | Shumakov et al. |
| 3,570,014 | A * | 3/1971 | Hancock ............... A61F 2/2418 623/2.18 |
| 3,574,865 | A | 4/1971 | Hamaker |
| 3,755,823 | A * | 9/1973 | Hancock ............... A61F 2/2418 623/2.18 |
| 3,839,741 | A | 10/1974 | Haller |
| 4,035,849 | A | 7/1977 | Angell et al. |
| 4,078,468 | A | 3/1978 | Civitello |
| 4,079,468 | A | 3/1978 | Liotta et al. |
| 4,084,268 | A | 4/1978 | Ionescu et al. |
| 4,106,129 | A * | 8/1978 | Carpentier ............ A61F 2/2418 623/2.18 |
| 4,172,295 | A | 10/1979 | Batten |
| 4,217,665 | A | 8/1980 | Bex et al. |
| 4,218,782 | A | 8/1980 | Rygg |
| 4,259,753 | A | 4/1981 | Liotta et al. |
| 4,340,091 | A | 7/1982 | Skelton et al. |
| 4,343,048 | A | 8/1982 | Ross et al. |
| 4,364,126 | A | 12/1982 | Rosen et al. |
| 4,388,735 | A | 6/1983 | Ionescu et al. |
| 4,441,216 | A | 4/1984 | Ionescu et al. |
| 4,451,936 | A | 6/1984 | Carpentier et al. |
| 4,470,157 | A * | 9/1984 | Love .................... A61F 2/2412 623/2.15 |
| 4,490,859 | A | 1/1985 | Black et al. |
| 4,501,030 | A * | 2/1985 | Lane .................... A61F 2/2418 623/2.18 |
| 4,506,394 | A | 3/1985 | Bedard |
| 4,535,483 | A | 8/1985 | Klawitter et al. |
| 4,566,465 | A | 1/1986 | Arhan et al. |
| 4,605,407 | A | 8/1986 | Black et al. |
| 4,626,255 | A | 12/1986 | Reichart et al. |
| 4,629,459 | A | 12/1986 | Ionescu et al. |
| 4,680,031 | A | 7/1987 | Alonso |
| 4,687,483 | A | 8/1987 | Fisher et al. |
| 4,705,516 | A | 11/1987 | Barone et al. |
| 4,725,274 | A | 2/1988 | Lane et al. |
| 4,731,074 | A | 3/1988 | Rousseau et al. |
| 4,778,461 | A | 10/1988 | Pietsch et al. |
| 4,790,843 | A | 12/1988 | Carpentier et al. |
| 4,851,000 | A | 7/1989 | Gupta |
| 4,888,009 | A | 12/1989 | Lederman et al. |
| 4,914,097 | A | 4/1990 | Oda et al. |
| 4,960,424 | A | 10/1990 | Grooters |
| 4,993,428 | A | 2/1991 | Arms |
| 5,010,892 | A | 4/1991 | Colvin et al. |
| 5,032,128 | A | 7/1991 | Alonso |
| 5,037,434 | A * | 8/1991 | Lane .................... A61F 2/2418 623/2.18 |
| 5,147,391 | A | 9/1992 | Lane |
| 5,163,955 | A | 11/1992 | Love et al. |
| 5,258,023 | A | 11/1993 | Reger |
| 5,316,016 | A | 5/1994 | Adams et al. |
| 5,326,370 | A | 7/1994 | Love et al. |
| 5,326,371 | A | 7/1994 | Love et al. |
| 5,332,402 | A | 7/1994 | Teitelbaum |
| 5,360,014 | A | 11/1994 | Sauter et al. |
| 5,360,444 | A | 11/1994 | Kusuhara |
| 5,376,112 | A | 12/1994 | Duran |
| 5,396,887 | A | 3/1995 | Imran |
| 5,397,351 | A | 3/1995 | Pavonik et al. |
| 5,423,887 | A | 6/1995 | Love et al. |
| 5,425,741 | A | 6/1995 | Lemp et al. |
| 5,431,676 | A | 7/1995 | Dubrul et al. |
| 5,449,384 | A | 9/1995 | Johnson |
| 5,449,385 | A | 9/1995 | Religa et al. |
| 5,469,868 | A | 11/1995 | Reger |
| 5,488,789 | A | 2/1996 | Religa et al. |
| 5,489,296 | A | 2/1996 | Love et al. |
| 5,489,297 | A * | 2/1996 | Duran .................. A61F 2/2418 623/2.13 |
| 5,489,298 | A | 2/1996 | Love et al. |
| 5,500,016 | A | 3/1996 | Fisher |
| 5,533,515 | A | 7/1996 | Coller et al. |
| 5,549,665 | A * | 8/1996 | Vesely .................. A61F 2/2409 623/2.14 |
| 5,562,729 | A | 10/1996 | Purdy et al. |
| 5,571,215 | A | 11/1996 | Sterman et al. |
| 5,573,007 | A | 11/1996 | Bobo, Sr. |
| 5,578,076 | A | 11/1996 | Krueger et al. |
| 5,584,803 | A | 12/1996 | Stevens et al. |
| 5,618,307 | A | 4/1997 | Donlon et al. |
| 5,626,607 | A | 5/1997 | Malecki et al. |
| 5,628,789 | A | 5/1997 | Vanney et al. |
| 5,693,090 | A | 12/1997 | Unsworth et al. |
| 5,695,503 | A | 12/1997 | Krueger et al. |
| 5,713,952 | A | 2/1998 | Vanney et al. |
| 5,716,370 | A | 2/1998 | Williamson, IV et al. |
| 5,728,064 | A | 3/1998 | Burns et al. |
| 5,728,151 | A | 3/1998 | Garrison et al. |
| 5,735,894 | A | 4/1998 | Krueger et al. |
| 5,752,522 | A | 5/1998 | Murphy |
| 5,755,782 | A | 5/1998 | Love et al. |
| 5,766,240 | A | 6/1998 | Johnson |
| 5,800,527 | A | 9/1998 | Jansen et al. |
| 5,814,097 | A | 9/1998 | Sterman et al. |
| 5,814,098 | A | 9/1998 | Hinnenkamp et al. |
| 5,824,064 | A | 10/1998 | Taheri |
| 5,824,068 | A | 10/1998 | Bugge |
| 5,840,081 | A | 11/1998 | Andersen et al. |
| 5,848,969 | A | 12/1998 | Panescu et al. |
| 5,855,563 | A | 1/1999 | Kaplan et al. |
| 5,855,601 | A | 1/1999 | Bessler et al. |
| 5,855,801 | A | 1/1999 | Lin et al. |
| 5,891,160 | A | 4/1999 | Williamson, IV et al. |
| 5,895,420 | A * | 4/1999 | Mirsch, II ............ A61F 2/2409 623/2.38 |
| 5,902,308 | A | 5/1999 | Murphy |
| 5,908,450 | A | 6/1999 | Gross et al. |
| 5,919,147 | A | 7/1999 | Jain |
| 5,921,934 | A | 7/1999 | Teo |
| 5,921,935 | A | 7/1999 | Hickey |
| 5,924,984 | A | 7/1999 | Rao |
| 5,928,281 | A * | 7/1999 | Huynh .................. A61F 2/2412 623/2.14 |
| 5,957,949 | A | 9/1999 | Leonhardt et al. |
| 5,972,004 | A | 10/1999 | Williamson, IV et al. |
| 5,984,959 | A | 11/1999 | Robertson et al. |
| 5,984,973 | A | 11/1999 | Girard et al. |
| 6,010,531 | A | 1/2000 | Donlon et al. |
| 6,042,554 | A | 3/2000 | Rosenman et al. |
| 6,042,607 | A | 3/2000 | Williamson, IV et al. |
| 6,066,160 | A | 5/2000 | Colvin et al. |
| 6,074,418 | A | 6/2000 | Buchanan et al. |
| 6,081,737 | A | 6/2000 | Shah |
| 6,083,179 | A | 7/2000 | Oredsson |
| 6,099,475 | A | 8/2000 | Seward et al. |
| 6,102,944 | A | 8/2000 | Huynh et al. |
| 6,106,550 | A | 8/2000 | Magovern et al. |
| 6,110,200 | A | 8/2000 | Hinnenkamp |
| 6,117,091 | A | 9/2000 | Young et al. |
| 6,126,007 | A | 10/2000 | Kari et al. |
| 6,162,233 | A | 12/2000 | Williamson, IV et al. |
| 6,168,614 | B1 | 1/2001 | Andersen et al. |
| 6,176,877 | B1 | 1/2001 | Buchanan et al. |
| 6,197,054 | B1 | 3/2001 | Hamblin, Jr. et al. |
| 6,217,611 | B1 | 4/2001 | Klostermeyer |

(56) References Cited

U.S. PATENT DOCUMENTS

| | | |
|---|---|---|
| 6,231,561 B1 | 5/2001 | Frazier et al. |
| 6,241,765 B1 | 6/2001 | Griffin et al. |
| 6,245,102 B1 | 6/2001 | Jayaraman |
| 6,264,611 B1 | 7/2001 | Ishikawa et al. |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,328,727 B1 | 12/2001 | Frazier et al. |
| 6,350,282 B1 * | 2/2002 | Eberhardt ............ A61F 2/2412 623/2.14 |
| 6,371,983 B1 | 4/2002 | Lane |
| 6,375,620 B1 | 4/2002 | Oser et al. |
| 6,402,780 B2 | 6/2002 | Williamson, IV et al. |
| 6,425,916 B1 | 7/2002 | Garrison et al. |
| 6,440,164 B1 | 8/2002 | Di Matteo et al. |
| 6,454,799 B1 * | 9/2002 | Schreck ............ A61F 2/2433 623/2.14 |
| 6,458,153 B1 | 10/2002 | Bailey et al. |
| 6,461,382 B1 * | 10/2002 | Cao ............ A61F 2/2409 623/2.19 |
| 6,468,305 B1 | 10/2002 | Otte |
| 6,478,819 B2 | 11/2002 | Moe |
| 6,491,624 B1 | 12/2002 | Lotfi |
| 6,558,418 B2 | 5/2003 | Carpentier et al. |
| 6,582,462 B1 | 6/2003 | Andersen et al. |
| 6,585,766 B1 | 7/2003 | Huynh et al. |
| 6,652,578 B2 | 11/2003 | Bailey et al. |
| 6,682,559 B2 | 1/2004 | Myers et al. |
| 6,685,739 B2 | 2/2004 | DiMatteo et al. |
| 6,730,118 B2 | 5/2004 | Spenser et al. |
| 6,733,525 B2 | 5/2004 | Yang et al. |
| 6,764,508 B1 | 7/2004 | Roehe et al. |
| 6,767,362 B2 | 7/2004 | Schreck |
| 6,773,457 B2 | 8/2004 | Ivancev et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,805,711 B2 | 10/2004 | Quijano et al. |
| 6,893,459 B1 | 5/2005 | Macoviak |
| 6,893,460 B2 | 5/2005 | Spenser et al. |
| 6,908,481 B2 | 6/2005 | Cribier |
| 6,939,365 B1 | 9/2005 | Fogarty et al. |
| 6,945,997 B2 * | 9/2005 | Huynh ............ A61F 2/2412 623/2.17 |
| 7,011,681 B2 | 3/2006 | Vesely |
| 7,018,404 B2 | 3/2006 | Holmberg et al. |
| 7,025,780 B2 | 4/2006 | Gabbay |
| 7,070,616 B2 | 7/2006 | Majercak et al. |
| 7,097,659 B2 | 8/2006 | Woolfson et al. |
| 7,101,396 B2 | 9/2006 | Artof et al. |
| 7,137,184 B2 * | 11/2006 | Schreck ............ A61F 2/2412 29/469 |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| RE40,377 E | 6/2008 | Williamson, IV et al. |
| 7,399,315 B2 * | 7/2008 | Iobbi ............ A61F 2/9525 623/2.14 |
| 7,422,603 B2 | 9/2008 | Lane |
| 7,513,909 B2 | 4/2009 | Lane et al. |
| 7,556,647 B2 | 7/2009 | Drews et al. |
| 7,569,072 B2 | 8/2009 | Berg et al. |
| 7,758,640 B2 * | 7/2010 | Vesely ............ A61F 2/243 623/2.38 |
| 7,871,435 B2 * | 1/2011 | Carpentier ............ A61F 2/2418 623/2.14 |
| 7,871,436 B2 * | 1/2011 | Ryan ............ A61F 2/2436 623/1.15 |
| 7,998,151 B2 | 8/2011 | St. Goar et al. |
| 9,339,381 B2 * | 5/2016 | Johnson ............ A61F 2/2418 |
| 9,414,913 B2 * | 8/2016 | Beith ............ A61F 2/2409 |
| 9,693,862 B2 * | 7/2017 | Campbell ............ A61F 2/0095 |
| 10,441,415 B2 * | 10/2019 | Johnson ............ A61F 2/2418 |
| 11,135,057 B2 * | 10/2021 | Johnson ............ A61F 2/2418 |
| 11,266,499 B2 * | 3/2022 | Johnson ............ A61F 2/2409 |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0020074 A1 | 2/2002 | Love et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151933 A1 | 10/2002 | Garrison et al. |
| 2002/0173842 A1 | 11/2002 | Buchanan |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109922 A1 * | 6/2003 | Peterson ............ A61F 2/2409 623/2.4 |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0195620 A1 | 10/2003 | Huynh et al. |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Iobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0096739 A1 | 5/2005 | Cao |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |

(56) References Cited

U.S. PATENT DOCUMENTS

| | | |
|---|---|---|
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0228494 A1 | 10/2005 | Marquez |
| 2005/0234546 A1 | 10/2005 | Nugent et al. |
| 2005/0240263 A1 | 10/2005 | Fogarty et al. |
| 2005/0251252 A1 | 11/2005 | Stoble |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0241745 A1 | 10/2006 | Solem |
| 2006/0259136 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2006/0293745 A1 | 12/2006 | Carpentier et al. |
| 2007/0005129 A1 | 1/2007 | Damm et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0033543 A1 | 2/2008 | Gurskis et al. |
| 2008/0119875 A1 | 5/2008 | Ino et al. |
| 2008/0154356 A1 | 6/2008 | Obermiller et al. |
| 2008/0294248 A1 | 11/2008 | Yang et al. |
| 2008/0319543 A1 | 12/2008 | Lane |
| 2009/0036903 A1 | 2/2009 | Ino et al. |
| 2009/0157175 A1 | 6/2009 | Benichou |
| 2009/0192599 A1 | 7/2009 | Lane et al. |
| 2010/0049313 A1 | 2/2010 | Alon et al. |
| 2010/0185277 A1* | 7/2010 | Braido .................. A61F 2/2409 623/2.37 |
| 2012/0296418 A1 | 11/2012 | Bonyuet et al. |
| 2017/0000603 A1* | 1/2017 | Conklin ................ A61F 2/2409 |
| 2020/0060814 A1* | 2/2020 | Murphy ................ A61F 2/2475 |

FOREIGN PATENT DOCUMENTS

| | | | |
|---|---|---|---|
| EP | 0143246 A2 | 6/1985 | |
| EP | 2568924 B1 * | 1/2021 | ........... A61F 2/2409 |
| GB | 2149062 A | 6/1985 | |
| SU | 1116573 A1 | 7/1985 | |
| SU | 1697790 A1 | 12/1991 | |
| WO | 9213502 A1 | 8/1992 | |
| WO | 9742871 A1 | 11/1997 | |
| WO | WO-03034950 A1 * | 5/2003 | ........... A61F 2/2409 |
| WO | WO-2012018779 A2 * | 2/2012 | ........... A61F 2/2418 |
| WO | 2012047761 A2 | 4/2012 | |

* cited by examiner

HEART VALVES WITH INCREASED EFFECTIVE ORIFICE AREA

RELATED APPLICATIONS

The present application is a continuation of U.S. application Ser. No. 15/591,915, filed May 10, 2017, now U.S. Pat. No. 11,266,499, which is a continuation of U.S. application Ser. No. 14/488,728, filed Sep. 17, 2014, now U.S. Pat. No. 10,441,415, which claims the benefit of U.S. Application No. 61/880,688, filed Sep. 20, 2013, the entire disclosures all of which are incorporated by reference for all purposes.

FIELD OF THE INVENTION

The present invention relates to a prosthetic heart valve having increased flow area for enhanced flow and, more particularly, to a flexible leaflet valve with modified stent and leaflet structure that increases the effective orifice area for a given valve size.

BACKGROUND OF THE INVENTION

Heart valve disease continues to be a significant cause of morbidity and mortality, resulting from a number of ailments including rheumatic fever and birth defects. Currently, the primary treatment of aortic valve disease is valve replacement. Worldwide, approximately 300,000 heart valve replacement surgeries are performed annually, many involving mechanical heart valves composed of rigid, synthetic materials while the rest receive bioprosthetic heart valves which utilize biologically derived tissues for flexible fluid occluding leaflets. In general, bioprosthetic valve replacements have good hemodynamic performance and do not require the anticoagulation therapy necessary for mechanical heart valves.

Flexible leaflets used in heart valves are typically made from bioprosthetic homograft or xenograft materials. For example, the most successful bioprosthetic materials are whole porcine valves and separate leaflets made from bovine pericardium stitched together to form a tri-leaflet valve. In addition, flexible leaflets formed of polymeric, fiber-reinforced, and other synthetic materials have been proposed. The most common bioprosthetic valve construction includes three leaflets mounted around a peripheral support structure with free edges that project toward an outflow direction and meet or coapt in the middle of the flowstream.

Aortic stenosis is abnormal narrowing of the aortic valve characterized by a significantly higher than normal pressure gradient across the aortic valve. It follows that an important characteristic of a replacement aortic valve is minimal aortic pressure gradient, typically attained by increasing the effective orifice area through the valve. Solutions include placement of the prosthesis (sub-annular, intra-annular and supra-annular) in order to implant a prosthesis with the largest possible effective orifice area. Supra-annular placement (where the sewing cushion lies above the aortic annulus) is often preferred because usually a valve with a larger internal orifice diameter can be implanted. However, in patients with small aortic roots, either due to anatomy, physical stature, or severe calcification, only the smallest-sized valves (e.g., 19 mm) may be used. Sometimes an even smaller valve would be desirable, but valves smaller than 19 mm are not commercially available. Moreover, even with a supra-annular implant, the valve often does not maximize the flow orifice area.

In view of actual and perceived drawbacks associated with current bioprosthetic heart valves, a valve with an increased effective orifice area for a given valve size is desirable.

SUMMARY OF THE INVENTION

The present application provides a low pressure gradient prosthetic heart valve for implant in a human. The valve includes a wireform with undulating inflow cusps and outflow commissure posts to which flexible leaflets attach and coapt in a flow area.

One aspect of the present application is a prosthetic heart valve comprising a first cloth-covered undulating wireform having alternating cusps and commissures around a periphery. A second cloth-covered undulating wireform has alternating cusps and commissures around a periphery, and the cusps and commissures of the two wireforms are aligned with one another. A plurality of flexible leaflets have outer edges sandwiched between the cusps of the first and second cloth-covered undulating wireforms. In one embodiment, the flexible leaflets have commissure edges sandwiched between the commissures of the first and second cloth-covered undulating wireforms. A cloth tab on one of the wireforms may encompass a small piece of silicone ribbon at least at the cusps thereof to provide a sewing ring.

The first and second wireforms may have similar sizes and shapes, with the cusps curving in an inflow direction and the commissures defining upstanding commissure posts with inverted U-shapes projecting in an outflow direction. The first wireform may be slightly smaller in radius and shorter in axial dimension than the second wireform which is positioned outward from the first wireform except at the aligned commissures where the first wireform bends outward so that its commissures are radially outside the second wireform and provide sewing anchors for commissure tabs of the flexible leaflets. The flexible leaflets preferably have tabs that are sandwiched between the first and second wireforms at the aligned commissures. In one version, the tabs of the flexible leaflets wrap around the first wireform and are attached thereto at the aligned commissures.

In another embodiment, the cusps of both wireforms curve in an inflow direction and the commissures of the second wireform define upstanding commissure posts with inverted U-shapes projecting in an outflow direction, wherein the first wireform has truncated commissures of about one half the height of the commissures of the second wireform. The flexible leaflets may have commissure tabs that extend outward through the inverted U-shaped commissures of the second cloth-covered wireform and are secured to cloth tabs extending from the cloth covering the second wireform.

In another embodiment, a prosthetic heart valve comprises a cloth-covered undulating wireform with alternating cusps and commissures, the commissures extending generally axially in an outflow direction and defining inverted U-shaped commissure posts. A plurality of flexible leaflets have outer cusp edges that extend over the top of the cusps of the wireform, and each of the leaflets has a free-edge that, when implanted, moves back and forth in and out of the flow orifice and coapts with the free edges of the other leaflets. Each leaflet also has tabs at either end of the free edge that project radially outward under the inverted U-shaped commissure posts and are secured thereto along with a tab from an adjacent leaflet.

The outer cusp edge of each leaflet desirably interrupted by two inwardly-directed slits that each receive a portion of the wireform near the U-shaped commissures on either side of the leaflet to permit the leaflet tabs to pass under the U-shaped commissures. The inwardly-directed slits may terminate in a rounded hole to closely conform around the wireform. A reinforced strip of material may be attached around the rounded holes, or more generally around the termination of the slits.

In a further embodiment, a prosthetic heart valve comprises a cloth-covered undulating wireform with alternating cusps and commissures, the commissures extending generally axially in an outflow direction and defining inverted U-shaped commissure posts, with the commissures bent outward and then generally axially again. A plurality of flexible leaflets have outer cusp edges that extend over the top of the cusps of the wireform, and each of the leaflets has a free-edge that, when implanted, moves back and forth in and out of the flow orifice and coapts with the free edges of the other leaflets. Each leaflet having tabs at either end of the free edge that project radially outward around the outside of the inverted U-shaped commissure posts. A commissural clip extends over the top of each wireform and leaflet tab at the commissures and is sewn to the cloth-covered wireform and leaflet tabs to secure the leaflet tabs around the wireform. The commissural clips may have a closed oval shape. The cloth tab on the wireform preferably encompasses a small piece of silicone ribbon at least at the cusps thereof to provide a sewing ring.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

DETAILED DESCRIPTION OF THE PREFERRED EMBODIMENTS

The present application describes certain principles that may be used in conjunction or separately for fabricating flexible leaflet prosthetic heart valves to reduce the pressure gradient of blood through the valve orifice. As general statements of benefits obtained from such a valve: the valve should open properly upon forward flow with minimal gradient; the valve should close properly and completely upon reverse flow with little regurgitation; the support structure (e.g., wireform) of the valve should be able to withstand the fatigue stress during a large number of the valve open/close cycles and maintain structural integrity; and the flexible leaflets should withstand the structural stress and maintain the structural function of opening and closing without calcification or structural deterioration.

The desire for these attributes is not necessarily new in the field of prosthetic heart valve design, but valves constructed based on the principles described herein improve on each, in particular by increasing the effective flow orifice area through the valve for a given size. It should be understood that the characteristics of heart valves expressed herein may be implemented in a variety of different flexible leaflet valves. For example, though three- or tri-leaflet valves are the most common and most studied, only two or a greater number of leaflets may also be used. Also, the support frame, or structural skeleton, for the flexible leaflets may take a variety of forms in addition to those illustrated and described herein. The valve support frame may be relatively dimensionally stable, or configured to be collapsible for minimally-invasive delivery. Finally, materials and fabrication techniques may vary while still conforming any valve to the described desirable principles. In summary, the present application encompasses many valves that include one or more of these variable aspects, only limited by the appended claims.

As used herein, a "neutral position" or a "neutral configuration" means a configuration of a valve and/or a frame when the respective valve and/or frame is at-rest (e.g., still) and free from externally applied loads (e.g., pressure gradients through the valve, forces applied by retaining and/or delivery devices to retain the valve in a collapsed configuration), and is not biased toward any other shape.

Further, the term "wireform" refers to an elongated rod-like structure formed into a continuous shape defining a circumference around a flow orifice for supporting flexible leaflets in the various prosthetic valves herein. Typically a wireform has an undulating shape with alternating inflow cusps and outflow commissures; usually three each. The wireforms described herein may be machined from tubes or wires, or may be molded if made of a polymer. The continuous structure may be homogenous with no joints, or a crimp may be used to join two ends of a preformed wire. The cross-section may be round, oval, square or other suitable configuration.

A prosthetic heart valve 20 of the prior art shown in FIGS. 1-5 includes an inlet end 22 and an outlet end 24 (FIG. 3) separated along a generally vertical flow axis 26 through approximately the middle of the valve. (It should be noted that blood flow through a heart valve is not precisely like flow through a tubular pipe, and thus the term "flow axis" should be understood to be an approximation and refers generally to an axis through the center of the valve orifice.) A cloth-covered support frame includes an annular stent assembly 28 and an annular wireform 30. The support frame defines a periphery and flow orifice of the valve. Both the stent assembly 28 and wireform 30 include commissure posts that project generally axially in the outflow direction and combine to form commissures 32 of the valve when covered with fabric. Both stent assembly 28 and wireform 30 also include arcuate cusps that curve in the inflow direction in between each two commissures that combine to form valve cusps 34. In the illustrated embodiment, the stent assembly 28 includes two annular bands, an outer metallic band and an inner polyester band that extends up the commissures. Three flexible leaflets 36 couple to the support frame and extend inward therefrom. The leaflets 36 attach along an undulating line that follows the commissures 32 and cusps 34. A suture-permeable sewing ring 38 surrounds the inflow end of the valve 20 and, as shown, features a non-planar peripheral shape which undulates upward a short distance in the vicinity of the three commissures 32. A planar sewing ring 38 may also be used.

The leaflets 36 may be provided by a whole porcine valve, but are preferably formed individually from bioprosthetic material such as bovine pericardium. It should be noted that a number of advantages of the present application are independent of the type of flexible leaflet, though the maximum benefit will be obtained by using sheets of bovine pericardium trimmed to particular sizes and shapes, as will be explained. Although not presently used in commercial valves, synthetic material may also be used for the leaflets, and the term, "flexible leaflets" is meant to include such other materials.

The prosthetic heart valves illustrated in FIGS. 1-5 represents the construction of a Carpentier-Edwards mitral pericardial valve, one of the leading commercially available bioprosthetic valves, available from Edwards Lifesciences of Irvine, CA The assembly process for the Carpentier-Edwards valve includes sewing the pericardial leaflets 36 to a cloth-covered wireform 30, and then this subassembly is mounted to a cloth-covered stent assembly 28 having a silicone sewing ring 38 connected thereto with sutures. The cloth covering of each component and their subsequent assembly is elaborate and labor-intensive.

However, this particular valve construction has a proven track record, partly because of the highly durable configuration where the valve leaflets 36 connect to the valve commissures 32. With reference to the enlarged view in FIG. 5, the leaflets 36 extend underneath the wireform 30 and outward through adjacent wires at the commissures 32, and are sandwiched between the wireform and a cloth tab (not shown) provide on the stent assembly 28. Commissure tabs 40 of adjacent leaflets 36 project through the commissure regions of the wireform 30 and wrap around the commissure posts of the stent assembly 28. By wrapping the leaflet tabs 40 in this manner, and securing them on the exterior of the stent assembly 28, the relatively high inward forces imparted to the free edges of the leaflets 36 from when the leaflets close are distributed to the stent assembly 28 and wireform 30, not just to sutures connecting the leaflets to the surrounding structure.

Figure 1:
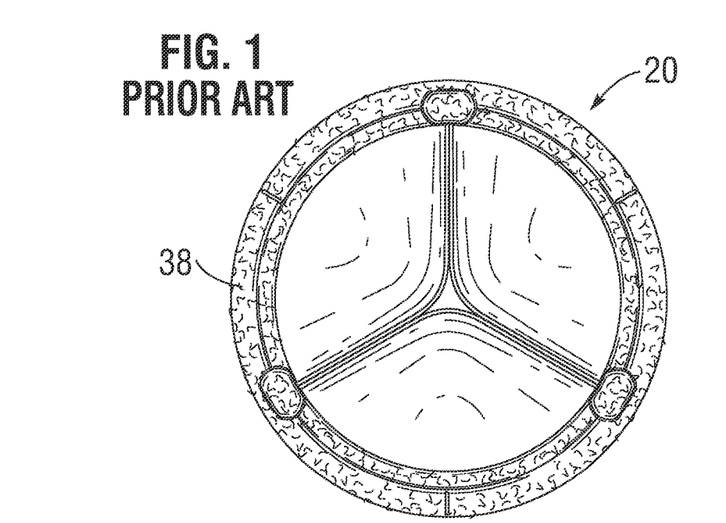
FIG. 1 is a plan view looking from the outflow end of a flexible leaflet bioprosthetic heart valve of the prior art.
Figure 2:
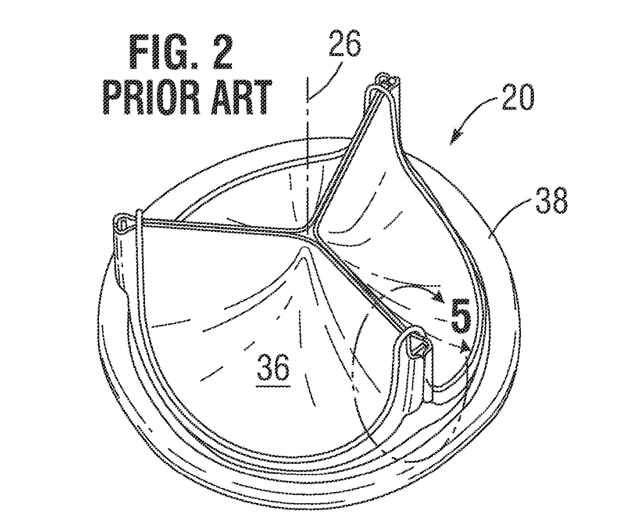
FIG. 2 is a perspective view of certain inner components of the heart valve of FIG. 1.
Figure 3:
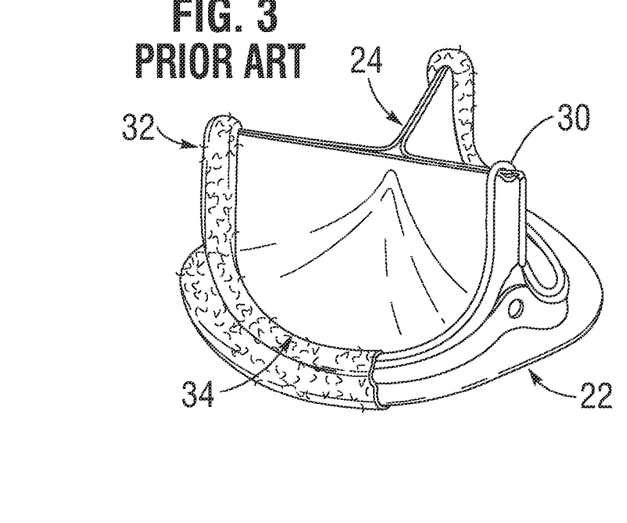
FIG. 3 is a partially cutaway view of the assembled heart valve of FIG. 1.
Figure 4:
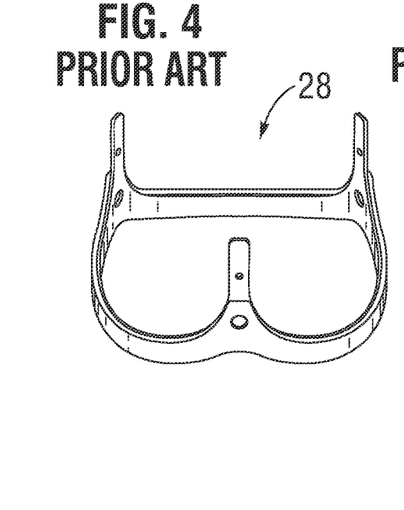
FIG. 4 is a perspective view of an inner stent assembly for the prior art heart valve of FIG. 1.
Figure 5:
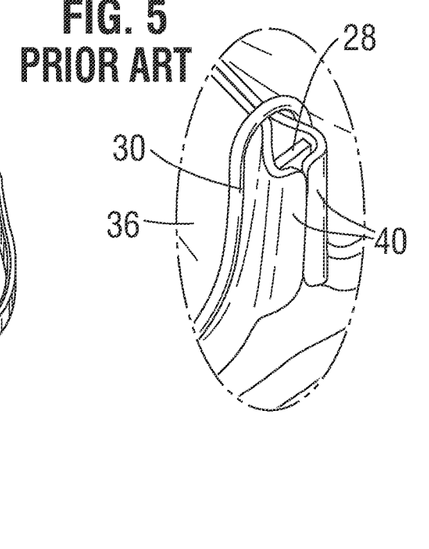
FIG. 5 is an enlarged perspective view of a commissure region of the heart valve of FIG. 1 with cloth coverings removed for clarity.

FIG. 1A shows the bioprosthetic heart valve 20 with the leaflets 36 closed. In use, the leaflets 36 open or separate from blood flow from the inflow end 22 to the outflow end 24, or in the outflow direction. Typical valves of the prior art have relatively floppy leaflets 36 that generally effectively coapt or meet in the flow orifice during the back flow portion of the flow cycle, as in FIGS. 1-3. The commissures 32 usually tilt somewhat inwardly relative to the central flow axis 26 from their inflow to their outflow ends so as to define a surface of revolution that surrounds a converging conical volume. This arrangement provides a flow constriction wherein the size of the orifice provided by the commissure posts 32 and leaflets 36 in the valve open state is smaller than the generally circular orifice defined at the inflow end 22. The combination of the generally conical flow column and typical valve assembly introduces flow restrictions that increase the fluid pressure gradient through the valve as opposed to a smooth cylinder, or idealized pipe flow.

Figures 6, 7, 8:
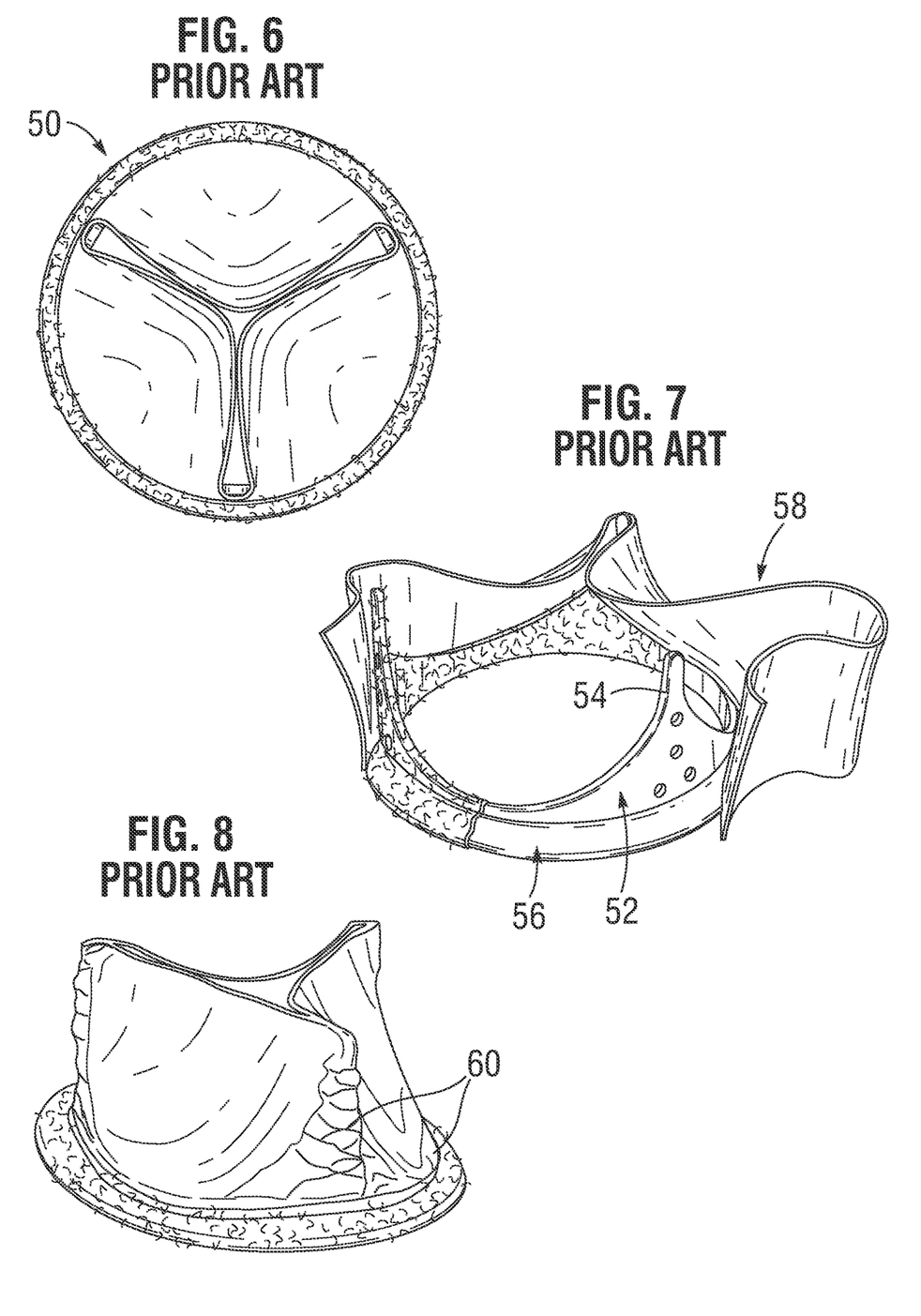
FIG. 6 is a plan view looking from the outflow end of an alternative flexible leaflet bioprosthetic heart valve of the prior art.
FIG. 7 is a partially disassembled perspective view of the heart valve of FIG. 6 showing certain internal components.
FIG. 8 is a perspective view of the assembled heart valve of FIG. 6.

FIGS. 6-8 illustrate construction of another commercially-available bioprosthetic heart valve 50, the Trifecta™ aortic valve available from St. Jude Medical of St. Paul, MN The valve 50 includes an inner polymer stent 52 having three generally axially-aligned commissure posts 54, and a sewing ring 56 surrounding the inflow end of the stent. A single sheet of bioprosthetic tissue 58 wraps around the outside of the stent 52 and is sewn thereto with sutures 60 along its commissure posts 54, and also along a peripheral line adjacent the sewing ring 56. The bioprosthetic tissue 58 is slightly taller than the stent commissure posts 54 to help provide enough free leaflet material ostensibly for good coaptation in the flow orifice. However, the extra leaflet material above the commissure posts 54 sometimes leads to leaflet prolapse, or poor coaptation and durability. Other so-called wrap-around designs of heart valves in the prior art include the Mitroflow valve from the Sorin Group of Milan, Italy, and the Ionescu-Shiley valve from Shiley Labs of Irvine, CA.

The present application provides prosthetic heart valves that are constructed to have proven durability and to maximize effective orifice area. More particularly, the heart valves described herein have flexible leaflets that are connected to a wireform/stent structure much like the Edwards Lifesciences Carpentier-Edwards valves described above with respect to FIGS. 1-5. At the same time, the flexible leaflets are attached over the top of at least one part of the wireform to increase the orifice area. The wireform may be provided in one or two parts.

Figure 9A:
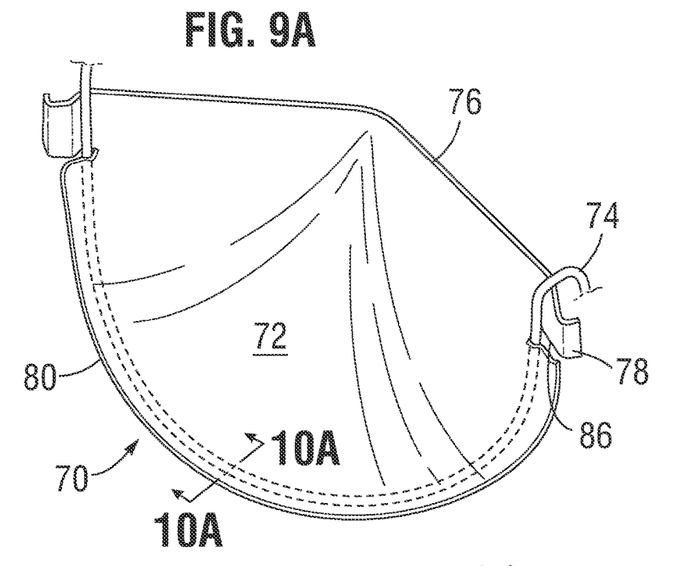
FIGS. 9A-9B are perspective views of a portion of a bioprosthetic heart valve of the present application shown closed and open, respectively.
Figure 10A:
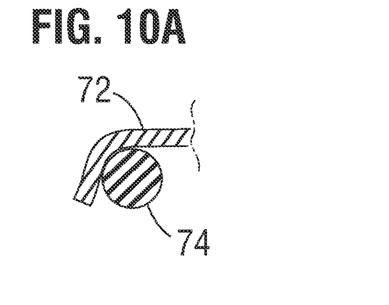

With reference now to FIG. 9A, a prosthetic heart valve 70 of the present application is represented by a single leaflet 72 (out of three) and its positional relationship to one third of a wireform 74. The wireform 74 extends in an undulating pattern (alternating cusps and commissures) around the entire heart valve, as with wireforms of the prior art. The reader will understand that additional constructional details such as the stent assembly or sewing ring are not shown for clarity. The leaflet 72 includes a free edge 76 that coapts within the orifice defined by the valve with the other leaflets (not shown). The free edge 76 of the leaflet terminates at either end in tabs 78. As with the Carpentier-Edwards heart valve described above, the leaflet tabs 78 extend outward underneath the inverted U-shaped commissures of the wireform 74 and preferably wrap around and are sewn to commissure posts of a stent structure (not shown). The outer leaflet 72 additionally has an arcuate cusp edge 80 that is secured around a cusp of the wireform 74, but instead of extending underneath the wireform and being sandwiched against the underlying stent structure, the leaflet 72 extends over the top of the wireform cusp 74, such as shown in FIG. 10A. Although not shown, the wireform 74 will again be cloth-covered, and the outer arcuate cusp edge 80 will be secured to an outer tab on the cloth covering with sutures, for example. In one embodiment, the outer cusp edge 80 wraps over and underneath the wireform 74 during assembly.

To enable this over-under attachment of the leaflet 72, a gap or slot 86 is provided between each leaflet tab 78 and the adjacent portion of the outer cusp edge 80. The slot 86 has a width that is approximately equal to the diameter of the wireform 74, and extends generally radially inward from the curved outer cusp edge 80 of the leaflet. To help prevent blood leakage in the area near the slot 86, additional fabric can be sewn around that area to secure the leaflet 72 as well as close any holes that might leak. An alternative to the slot 86 is a small hole in the leaflet 72 having a diameter approximately equal to the diameter of the wireform 74. In this embodiment, the "gap" between the tabs 78 and the cusp edge 80 can be a slit cut in the leaflet (i.e., the gap width is zero) from its cusp edge to the small hole. Alternatively, the slot 86 may be located within the tab 78 which helps facilitate attachment and conceal any opening that might leak.

Figures 9B, 9C, 10B, 10C:
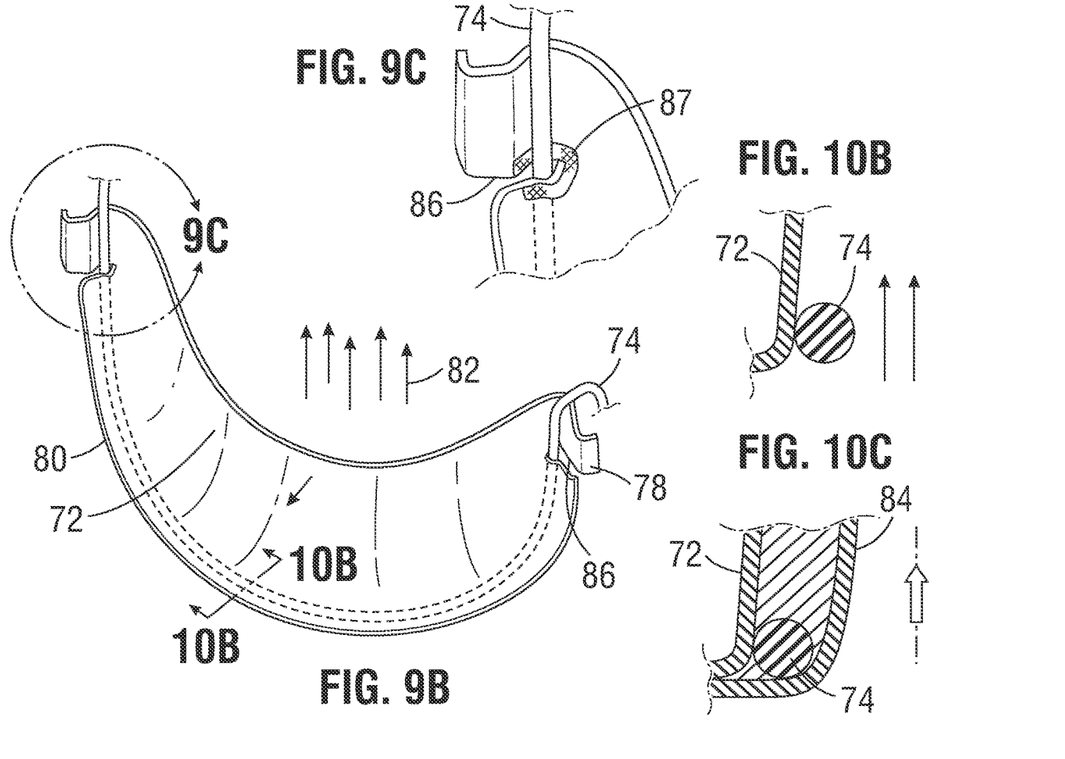
FIG. 9C is an enlargement of one corner of a leaflet.
FIGS. 10A-10B are radial sectional views through a cusp region of the heart valve of FIGS. 9A and 9B showing an exemplary attachment between flexible leaflets and wireform.
FIG. 10C is a radial sectional view similar to FIG. 10B and illustrating the difference in flow orifice area between attaching the flexible leaflets underneath and over the wireform.

In one embodiment, the slot 86 is reinforced to help prevent tearing. For example, FIG. 9C shows an enlargement of one corner of the leaflet where the area around the slot has a reinforced strip 87. The strip 87 may be an added layer of bioprosthetic tissue, or a section of fabric such as Dacron. Alternatively, the slot 86 may terminate in a rounded hole to closely conform around the wireform 74 and reduce points of high stress, as well as having the reinforced strip 87. Another possibility is to leave the portion of the leaflet 72 around the slot 86 much thicker than the rest of the leaflet, such as by cutting the leaflet from particular areas of the pericardial sac, or by thinning the rest of the leaflet.

It should also be noted that the length of the leaflet free edge 76 between the tabs 78 is designed to encourage full opening of the leaflet. If R is the wireform radius at the location of its commissures, then the length of the leaflet free edge 76 is equal to at least about $2\pi R/3$.

FIG. 9A illustrates the leaflet 72 in its closed position, with the free edge 76 bowed inward so that its midpoint lies essentially along a central flow axis through the valve and coapts with the other two leaflets. FIG. 10A shows the leaflet 72 extending inward over the wireform 74. Conversely, FIG. 9B shows the leaflet 72 in its open configuration with blood flow 82 indicated by upward arrows through the flow orifice. As can be seen in FIG. 10B, positioning the outer edge of the leaflet 72 over the top of the wireform 74 maximizes the effective orifice area by eliminating any impediment to flow caused by the leaflet 72 projecting inward from the wireform 74. FIG. 10C illustrates a leaflet 84 of the prior art attached underneath the wireform 74, and also shows the new arrangement with the leaflet 72 attached over the wireform. The region in between the two leaflets 72, 84 indicates the area in which flow may be restricted by the "under-the-wireform" leaflet.

Figure 11A:
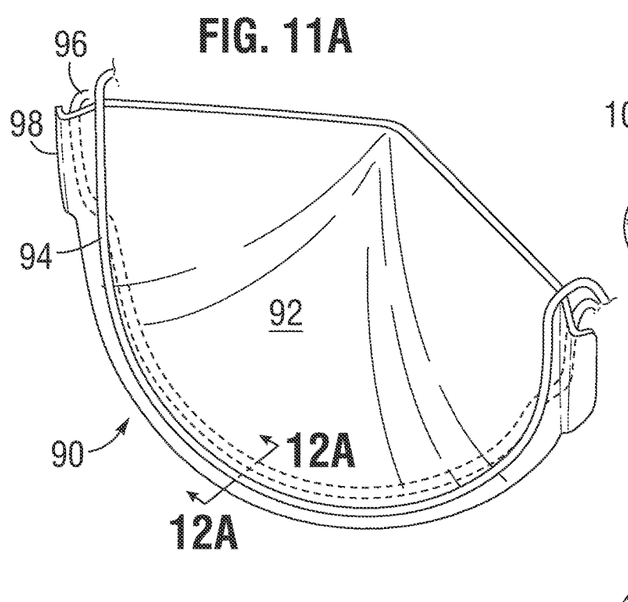
FIGS. 11A-11B are perspective views of a portion of an alternative dual-wireform bioprosthetic heart valve of the present application shown closed and open, respectively.
Figure 11B:
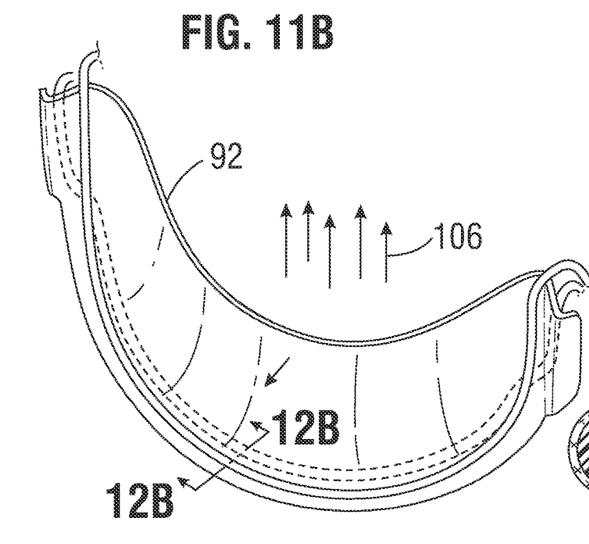
Figure 12A:
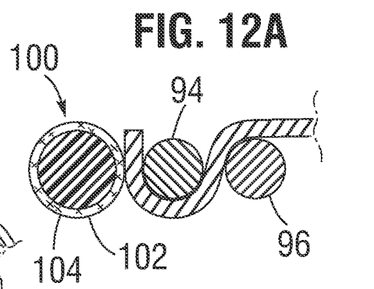
FIGS. 12A-12B are radial sectional views through a cusp region of the heart valve of FIGS. 11A and 11B showing an exemplary attachment between flexible leaflets and the dual wireforms.
Figure 12B:
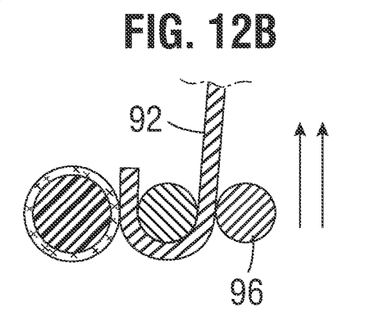
Figure 12C:
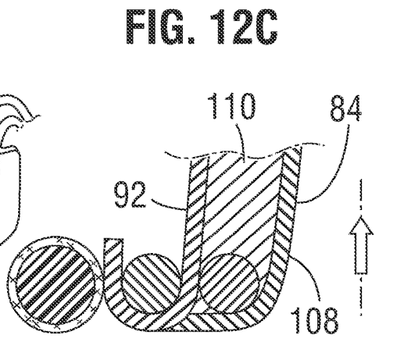
FIG. 12C is a radial sectional view similar to FIG. 12B and illustrating the difference in flow orifice area between attaching the flexible leaflets underneath and over an inner wireform.

In addition to a single-wire wireform such as shown at 74 above, the present application also contemplates a "sandwiched" configuration of a dual-wire wireform, such as shown in FIGS. 11-12. More particularly, a prosthetic heart valve 90 is again represented by a single leaflet 92 shown in its orientation relative to a wireform assembly of an outer wireform 94 and an inner wireform 96. Again, both of the wireforms 94, 96 extend around the periphery of the heart valve in an undulating pattern with cusps and commissures.

The overall profile of the inner wireform 96 is smaller in radius and shorter in axial dimension than the outer wireform 94. However, at the commissure regions, the inner wireform 96 bends outward so that it is radially outside the outer wireform 94 to serve as the sewing anchor for the leaflet tabs 98. That is, the commissures of the inner wireform 96 take the place of the commissure posts of a stent structure, as in the prior art. Adjacent leaflet tabs 98 wrap around the inner wireform 96 and are sewn together. The OD of the inner wireform 96 at the cusp region should be equal to the size of the valve. That is, each valve has an identified size, typically in odd 2 mm increments from 19-29 mm. The inner wireform 96 thus has a diameter at its cusps that is about 19 mm for a size 19 valve, and so on. The inner wireform 96 thus helps to maintain a leaflet opening area as large as the circular opening area of the inner wireform.

The outer wireform 94 follows a similar contour profile as existing wireforms of the prior art, though it has a larger diameter. The leaflet 92 is sandwiched between the two wireforms 94, 96 in the belly area. The leaflets 92 wrap over the inner wireform 96 and then under the outer wireform 94 which keeps the leaflet belly in place. The gap between the inner and outer wireforms 94, 96 in the belly region (center of the cusps) is therefore approximately equal to the thickness of the leaflet 92. In the commissure region, the leaflet tabs 98 pass under the inverted U-shaped commissures of the outer wireform 94, which thus keeps the leaflet tabs together so that the three leaflets maintain the coaptation when closed. The leaflet belly edges can be inserted underneath the outer wireform and then typically sewn together with a sewing ring (not shown). Although a sewing ring is used in conventional heart valves, some newer configurations eliminate it for various reasons. For example, some heart valves attach to the annulus through self-contained structure such as clamps, stents, or barbs, or are otherwise attached without (primarily) using sutures, which is the main purpose of a sewing ring. Also, a soft ring may be provided around the valve to seal against the surrounding annulus and prevent leakage around the valve, but it may not be a conventional sewing ring in that it is not used as the primary anchoring structure with sutures.

The two wireform assembly serves several purposes. The cusp region of the inner wireform 96 keeps the same contour profile and same circular opening diameter as the existing wireform from valves of the prior art. The inner wireform 96 thus helps to maintain a maximum opening profile since the leaflet rests on top of the inner wireform in the belly region. At the same time, the outer wireform 94 keeps the leaflet belly in place and maintains the leaflet tabs 98 together to enhance coaptation. Further, the inner wireform 96 bends outward at the commissures to provide the attachment structure for the leaflet tabs 98, thus eliminating one purpose for the stent structure in prior art valves. Indeed, the entire valve may include the two wireforms 94, 96 covered with cloth and sewn to the leaflets 92, plus a suture-permeable sewing ring 100 (See FIG. 12A) secured around the periphery of the wireform assembly. Again, the sewing ring is shown here as an example only, and may represent a sealing ring or may be eliminated altogether.

FIG. 12A illustrates an exemplary construction where the outer edge of the leaflet 92 is wrapped around the outer wireform 94 and the sewing ring 100 is secured therearound. Each of the wireforms 94, 96 will be covered with fabric, although that has been omitted for clarity. The fabric around the wireforms 94, 96 may be sewn to the sewing ring 100, which typically includes an inner silicone core 102 surrounded by fabric 104. FIG. 12A shows the valve and its closed position with the leaflet 92 caused by fluid backflow to move to the middle of the flow orifice and coapt against the other leaflets.

On the other hand, FIGS. 11B and 12B show the leaflet in an open configuration, with blood flow 106 indicated. Because the leaflet 92 extends over the top of the inner wireform 96, it does not present an impediment to blood flow and thus maximizes the effective orifice area. FIG. 12C again illustrates the position of a leaflet 108 that is attached underneath the inner wireform 96 in the open configuration of the valve. The region 110 in-between this leaflet 108 and a leaflet 92 that extend over the wireform 96 is the difference in orifice flow area which is gained by use of the present valve constructions.

Figure 13:
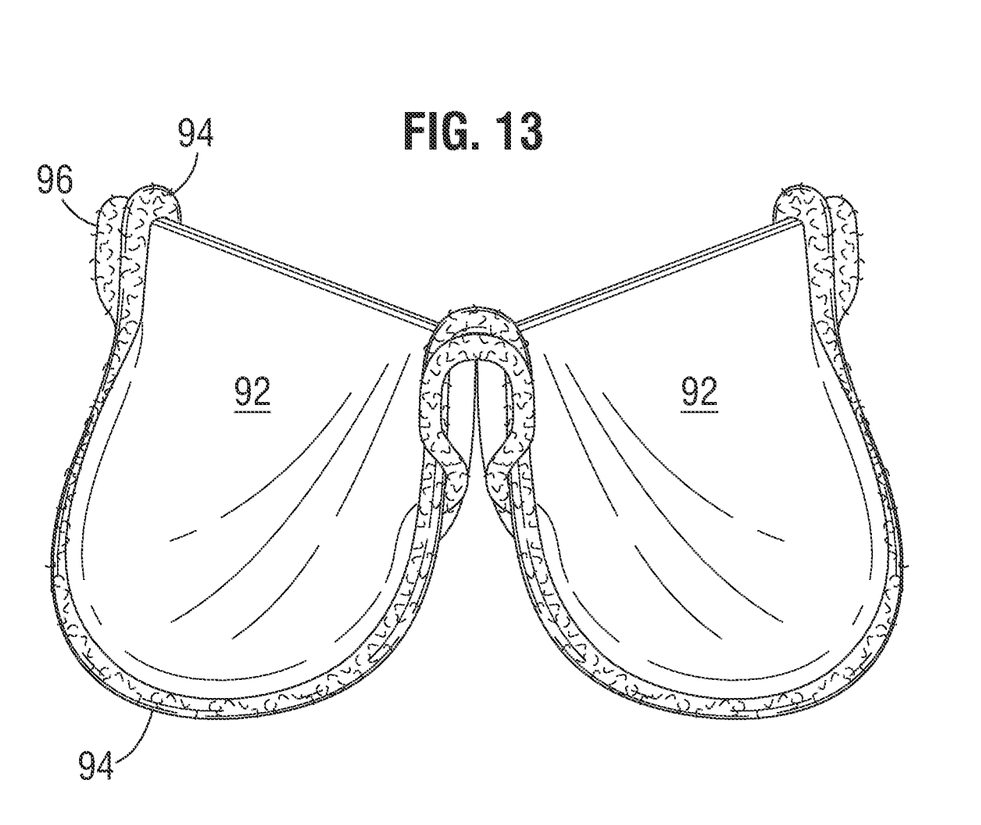
FIG. 13 is a perspective view of an assembled heart valve as in FIGS. 11A and 11B with dual wireforms which cross over each other at the commissure regions.

FIG. 13 is a perspective view of an assembled heart valve as in FIGS. 11A and 11B with the dual wireforms 94, 96 which cross over each other at the commissure regions. The outer wireform 94 is always observable, and the inner wireform 96 is covered by the leaflets except at commissure tips which bend to the outside of the outer wireform. The tabs of the leaflets 92 are sandwiched between the outer wireform 94 and inner wireform 96 at the commissural posts. In a preferred embodiment, the tabs of the leaflets 92 wrap around the inner wireform 96, which is not shown because the entire assembly is covered with fabric.

Figure 14:
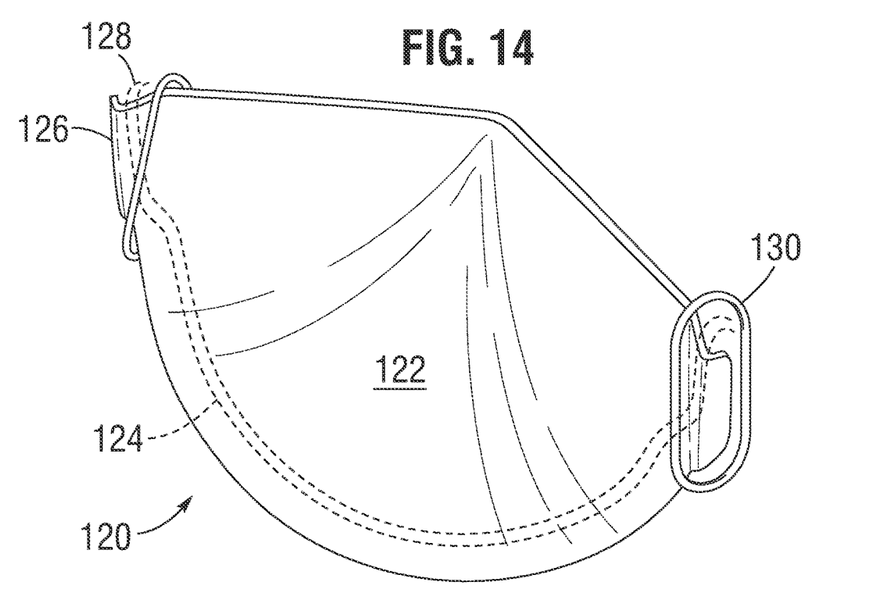
FIG. 14 is a perspective view of a still further prosthetic heart valve of the present application having a single wireform and clips at the commissure regions.

Another alternative prosthetic heart valve 120 is seen in FIG. 14. As with the first environment, there is a single-wire wireform 122 over which the cusp edges of each leaflet 124 attaches. Leaflet tabs 126 wrap around stent commissure posts 128 which are bent outward and then generally axially again to make room for a commissural clip 130. The clips 130 help maintain good leaflet coaptation while reducing stresses in the leaflet for better durability. Once again, because each leaflet 124 extends over the top of the wireform 122, the effective orifice area is maximized. Although not shown, cloth coverings around the wireform 122 and the clips 130 are sewn together to secure the assembly. The clips 130 are shown as closed ovals, though other configurations are possible.

Figure 15:
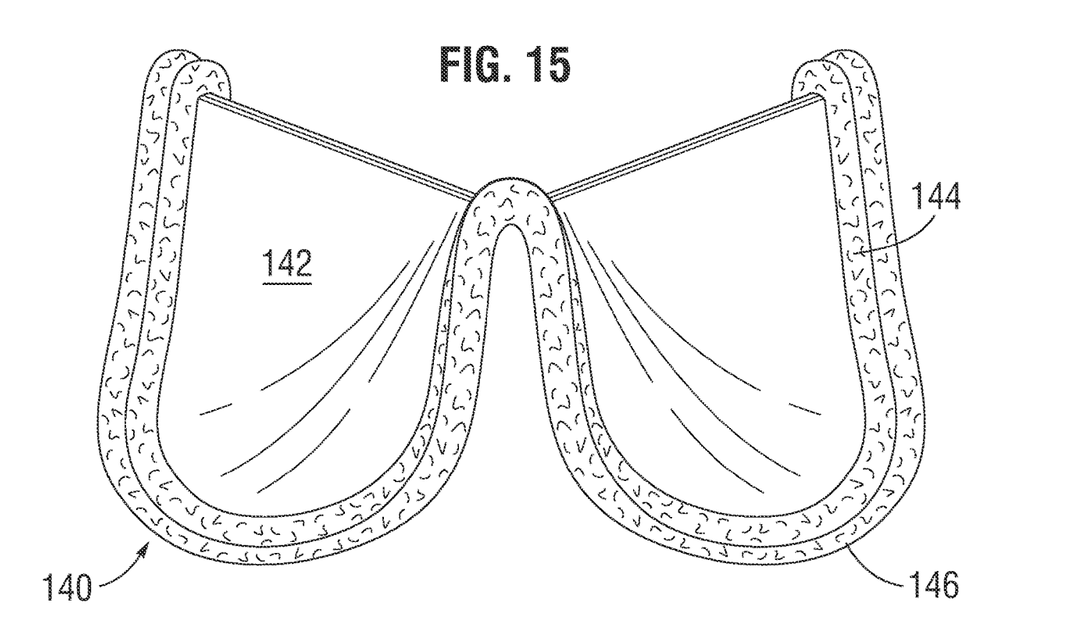
FIG. 15 is a perspective view of a dual-wireform prosthetic heart valve.

FIG. 15 is a subassembly of a dual-wireform prosthetic heart valve 140 with the leaflets 142 secured therein. An outer cloth-covered wireform 144 attaches under an inner cloth-covered wireform 146. Although not shown, a sewing ring may attach around the cusp portions of the wireforms 144, 146, with the gaps at the commissure portions of the wireforms filled-in with fabric or other such material to prevent leakage.

Figure 16:
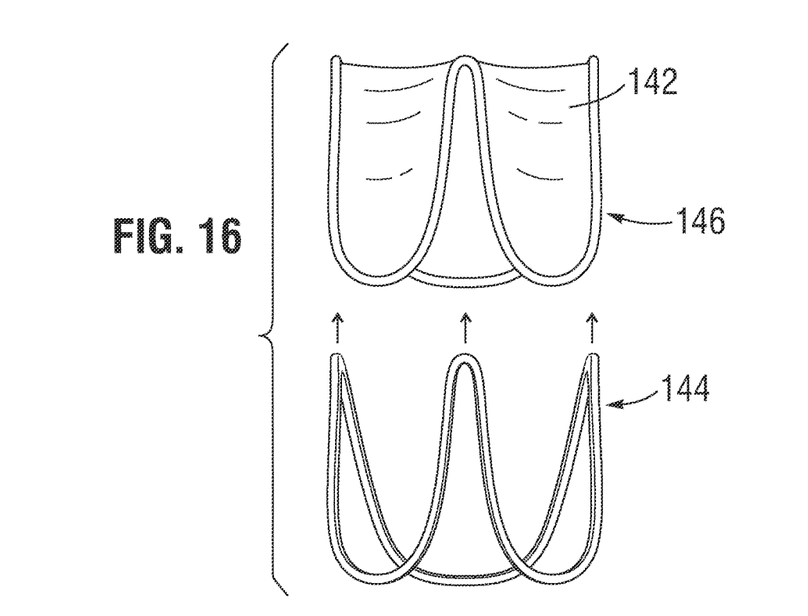
FIG. 16 illustrates one step in a procedure for assembling the dual-wireform prosthetic heart valve of FIG. 15.

The dual-wireform valve 140 of FIG. 15 may be assembled as seen in FIG. 16. More particularly, the outer or larger cloth-covered wireform 144 attaches underneath or around the inner cloth-covered wireform 146. Preferably, the flexible leaflets 142 are pre-attached to the inner wireform 146 as shown. The outer wireform 144 may align directly below the inner wireform 146, or may be slightly radially larger.

Figure 17A:
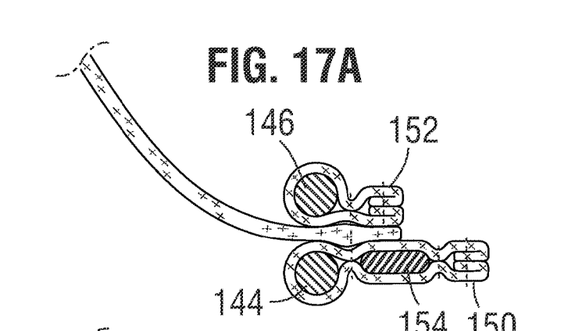
FIGS. 17A-17C are radial sectional views through cusps of a dual-wireform prosthetic heart valve of the present application.
Figure 17B:
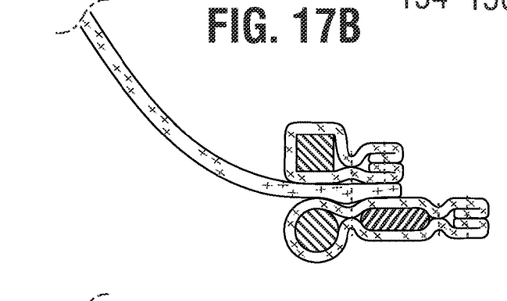
Figure 17C:
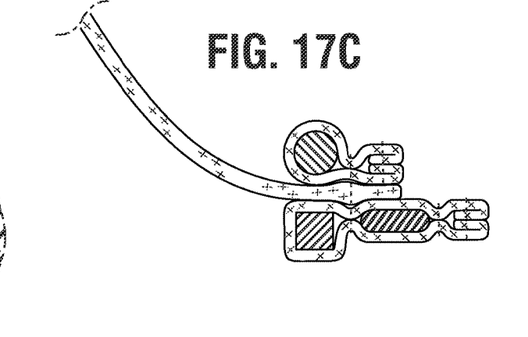

As seen in FIGS. 17A-17C, the wireforms 144, 146 may be round or square in cross-section, or have another polygonal shape. Wireforms with square or rectangular cross-sections may lock together or stay axially aligned better than wireforms with round cross-sections. It should be noted that the wire diameters of both the inner and outer wireforms 144, 146 can be the same or different so as to change the spring rate, commissure deflection rate, and valve function.

In a preferred embodiment, the wireforms for any of the valves disclosed herein are a cobalt-chromium-nickel alloy such as Elgiloy. However, the wireforms can be formed of any semi-rigid (meaning not floppy) metallic or polymeric materials that possess sufficient elasticity to maintain their shape for delivery and implant yet are capable of flexing to a small degree post-implant from natural systolic-diastolic forces. Elgiloy, stainless steel, titanium, and Nitinol are all possible metallic materials, and various polyester or nylon synthetic materials are options.

As seen in FIGS. 17A-17C, a cloth tab 150 attached to the outer wireform 144 extends beyond a cloth tab 152 attached to the inner wireform 146. A small piece of silicone tubing or ribbon 154 may be added to the larger cloth tab 150 at least at the cusps of the wireform 144 to provide a sewing ring or sorts and larger target for needle penetration. The leaflets 142 are sandwiched between the two wireforms 144, 146, and are sewn thereto through the adjacent cloth tabs 150, 152. It should be noted that the cross-sectional shapes of the wireforms 144, 146 are shown in a variety of ways to emphasize possible combinations; both rounded, one square and one rounded, etc.

Figure 18A:
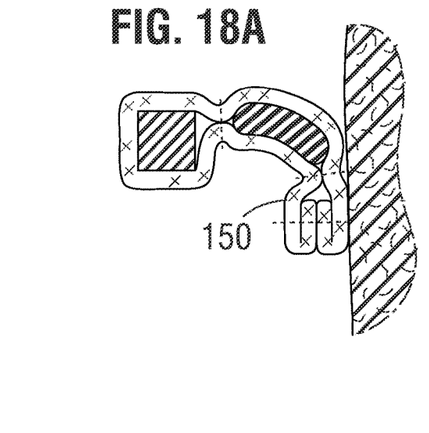
FIGS. 18A and 18B illustrate two different implantation configurations for the dual-wireform prosthetic heart valves disclosed herein.
Figure 18B:
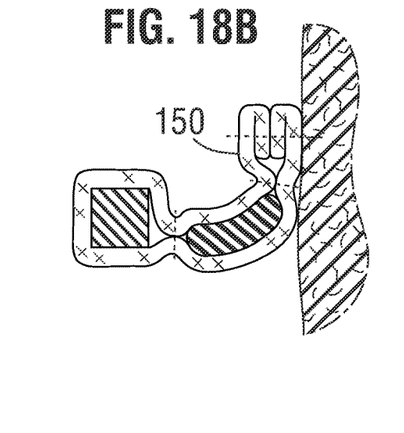

In an exemplary implementation procedure, the valve 140 would directly attach to the wall of the aorta using the larger cloth tab 150 of the outer wireform 144. The tab 150 can be bent downward as in FIG. 18A, or upward as in FIG. 18B. The cloth tab 150 extends up and down the wireforms 144, 146, and thus follows the natural scalloped shape of the aortic wall. Although not shown, the attachment of the leaflets 142 at the commissures may be configured the same as any of the other dual-wireform valves disclosed herein, such as by bending the inner wireform 146 radially outward and wrapping leaflet tabs around it.

The highly flexible valve provided by the dual wireform assembly of FIGS. 15-18 greatly improves hemodynamics over aortic valves currently on the market having relatively rigid annular frames. The attachment up and down the commissures at the aorta maximizes the size of valve which can be implanted. It is also anticipated that this valve will have similar durability properties compared to those currently produced since the leaflets are supported from above and below by wireforms. Moreover, the valve 140 also realizes significant cost savings over currently manufactured valves. The relatively simple assembly of the dual wireforms as seen in FIG. 16 replaces the labor-intensive stitching typically required with numerous cloth-covered components.

Moreover, the dual-wireform valve 140 of FIG. 15 eliminates any rigid annular components of the heart valve, which is a fairly standard construction in commercial valves. Consequently, the three cusp portions of the wireforms 144, 146 are relatively free to expand and contract with the surrounding annulus and ascending aorta, thus improving hemodynamics. Furthermore, the highly flexible nature of the dual-wireform valve 140 facilitates a subsequent valve-in-valve procedure. Over time, prosthetic heart valves may experience reduced performance from calcification, for example, requiring replacement. One technique available is to implant an expandable valve directly inside the existing prosthetic valve. However, prior surgical valves typically have rigid annular internal frames or stents, so that the second valve cannot be expanded to the same orifice diameter. With the highly flexible dual-wireform valve 140, however, a subsequently implanted valve can be balloon expanded and force the first valve open. The cusp regions separate from the outward force, and the new valve will then expand to a suitable diameter without sacrificing any flow volume from the valve-in-valve procedure.

Figure 19A:
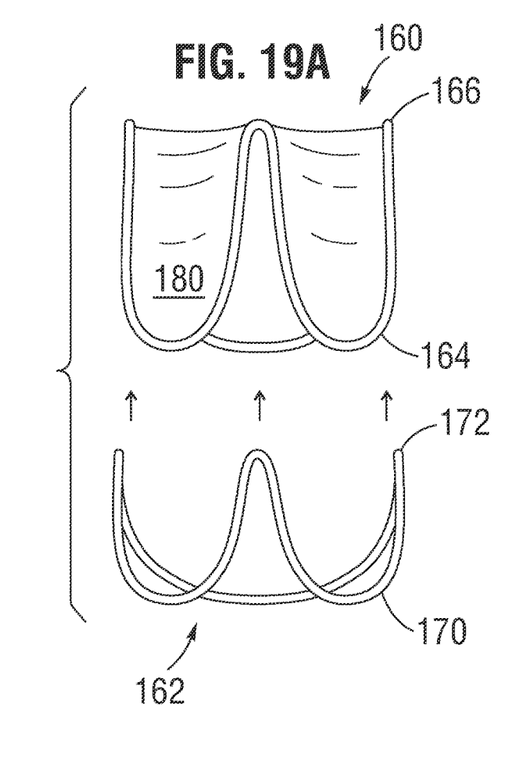
FIGS. 19A and 19B are exploded and assembled views of two wireforms in an alternative dual-wireform prosthetic heart valve having a truncated lower wireform.
Figure 19B:
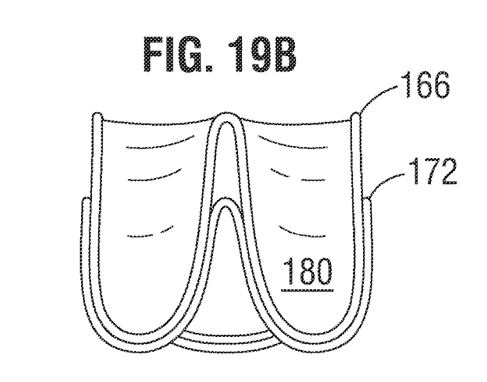

FIGS. 19A and 19B show upper and lower wireforms 160, 162 for use in an alternative dual-wireform prosthetic heart valve. The upper wireform 160 has substantially the same configuration as those described above, with alternating arcuate cusps 164 and inverted U-shaped commissures 166. The lower wireform 162 on the other hand is truncated with three arcuate valleys 170 that match the shape of the upper wireform cusps 164 and three upstanding peaks 172 that extend only partway up the upper wireform commissures 166. In one embodiment, the height of the lower wireform 162 at the peaks 172 is about one half the height of the upper wireform 160 at the commissures 166. The assembled wireform structure seen in FIG. 19B shows the upper wireform commissures 166 generally unsupported by the lower wireform 162. Flexible leaflets 180 are supported by the combination of the upper and lower wireforms 160, 162, and are shown schematically without connecting structure merely to indicate their placement. As will be explained, both the upper and lower wireforms 160, 162 are typically covered with fabric to facilitate their attachment to each other and to the leaflets 180 using sutures or the like.

In a similar manner as the version of FIG. 15, a sewing ring (not shown) may attach around the cusp portions of the wireforms 160, 162, with gaps at the commissures regions filled-in with fabric or other such material to prevent leakage. For instance, a sewing ring such as the cloth tab 150 seen in FIGS. 18A and 18B may be used. Peripheral edges of the flexible leaflets 180 are desirably sandwiched between the two wireforms 160, 162 at least in the cusp regions, much like was described above with respect to FIGS. 17A-17C.

Figures 20A, 20B:
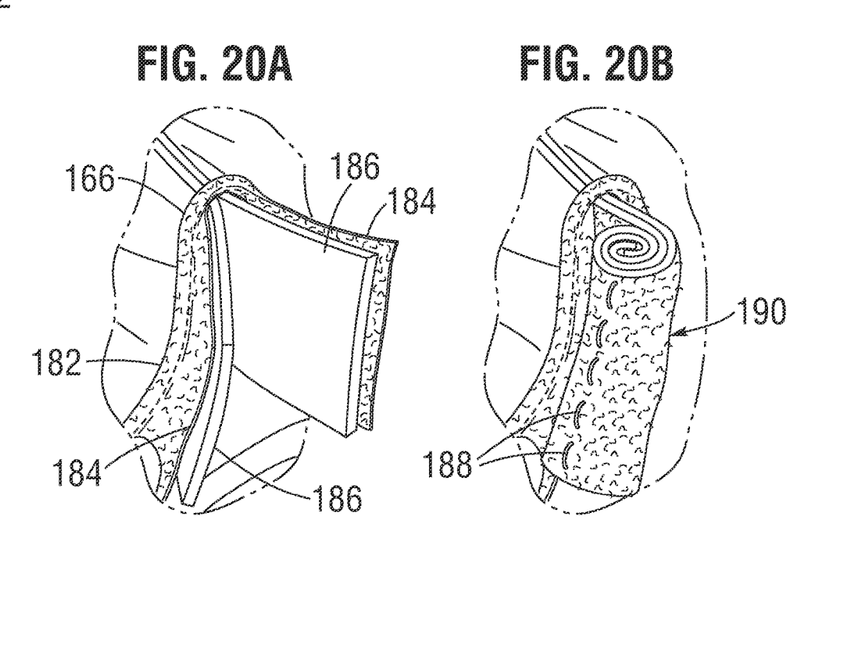
FIGS. 20A and 20B are detailed views of a commissure post region of an assembled heart valve of FIGS. 19A and 19B showing one way to attach flexible leaflets to an upper wireform.

FIGS. 20A and 20B show a commissure post region of an assembled heart valve illustrating a manner of attaching the flexible leaflets 180 to the upper wireform commissures 166. In particular, a cloth (polyester fabric) covering 182 that extends along the length of the upper wireform 160 includes tab extensions 184 at the upper regions of the commissures 166 to which leaflet tabs 186 are sewn. The leaflet tabs 186 project radially outward between the spaced wires of the commissures 166 and between the cloth tab extensions 184. FIG. 20A shows a partial assembly to make clear the connection, and the combined tab of the cloth tab extensions 184 and leaflet tabs 186 are preferably rolled or folded and sewn with sutures 188 into a bundle 190 outside of the commissures 166 as seen in FIG. 20B. This bundle 190 is larger than the gap between the spaced wires of the commissures 166, and thus the leaflet tabs 186 are secured to the commissures 166 and have little stress imparted to the connecting sutures 188 because of the bundled configuration. Optionally, a small insert (not shown) of stiffer cloth or polymer may be rolled up within the bundle 190 for additional bulk to maintain the bundle on the outside of the commissures 166.

While the invention has been described in its preferred embodiments, it is to be understood that the words which have been used are words of description and not of limitation. Therefore, changes may be made within the appended claims without departing from the true scope of the invention.

What is claimed is:

1. A prosthetic heart valve, comprising:
a first rod-like undulating wireform formed in a continuous shape defining alternating cusps and commissures and having a cloth covering, wherein the commissures extend generally axially in an outflow direction and define inverted U-shaped commissure posts and each cusp is arcuate and extends in an inflow direction spanning a distance between each two commissures, the first wireform circumscribing a flow orifice therewithin for blood flow; and
a plurality of separate flexible leaflets having outer cusp edges that extend over an outflow side of the cusps of the first wireform and attach to the cloth covering at the cusps, adjacent leaflets being secured to each other at the commissures, each of the leaflets having a free edge that, when implanted, alternately moves into and out of the flow orifice from fluid forces associated with cardiac blood flow cycles, wherein the free edge of each leaflet coapts with the free edges of the other leaflets to close the valve and the attachment of each leaflet over the outflow side of the first wireform cusps maximizes an effective orifice area by eliminating any impediment to flow caused by the leaflets projecting inward from the first wireform at the cusps.

2. The heart valve of claim 1, wherein the first wireform defines a radius at the commissures, and a length of each leaflet free edge is equal to at least about $2\pi R/3$.

3. The heart valve of claim 1, wherein each leaflet has tabs at either end of the free edge that project radially outward under the inverted U-shaped commissure posts and are secured thereto along with a tab from an adjacent leaflet.

4. The heart valve of claim 1, wherein the outer cusp edge of each leaflet is interrupted by two inwardly-directed slits that each receive a portion of the first wireform near the U-shaped commissures on either side of the leaflet to permit the leaflet tabs to pass under the U-shaped commissures.

5. The heart valve of claim 4, wherein the inwardly-directed slits terminate in a rounded hole to closely conform around the first wireform.

6. The heart valve of claim 5, further including a reinforced strip of material attached around the rounded holes.

7. The heart valve of claim 4, wherein the inwardly-directed slits terminate in a reinforced strip.

8. The heart valve of claim 1, wherein each leaflet has tabs at either end of the free edge that project radially outward around the outside of the inverted U-shaped commissure posts.

9. The heart valve of claim 8, further including a plurality of commissural clips each of which extends over the top of the first wireform and leaflet tabs at the commissures and is sewn to the cloth covering the first wireform and leaflet tabs to secure the leaflet tabs around the first wireform.

10. The heart valve of claim 9, wherein the commissural clips have a closed oval shape.

11. The heart valve of claim 9, wherein a cloth tab on the first wireform encompasses a small piece of silicone ribbon at least at the cusps thereof to provide a sewing ring.

12. The heart valve of claim 8, further including a second rod-like undulating wireform defining alternating cusps and commissures and having a cloth covering, wherein the commissures extend generally axially in an outflow direction and define inverted U-shaped commissure posts and each cusp is arcuate and extends in an inflow direction spanning a distance between each two commissures, the cusps and commissures of the first and second wireforms being circumferentially aligned with one another, wherein the leaflet outer cusp edges are sandwiched between the cusps of the first and second wireforms.

13. The heart valve of claim 12, wherein the first wireform is slightly smaller in radius than the second wireform which is positioned outward from the first wireform except at the aligned commissures where the first wireform bends outward so that its commissures are radially outside the second wireform and provide sewing anchors for the leaflets.

14. The heart valve of claim 13, wherein the leaflets each have tabs at either end of the free edge that are sandwiched between the first and second wireforms at the aligned commissures.

15. The heart valve of claim 14, wherein the tabs of the leaflets wrap around the first wireform and are attached thereto at the aligned commissures.

16. The heart valve of claim 13, wherein the leaflets have commissure tabs that extend outward through the inverted U-shaped commissures of the second wireform and are secured around the commissures of the first wireform along with a tab from an adjacent leaflet.

17. The heart valve of claim 13, wherein the commissures of the first wireform are shorter in height than the commissures of the second wireform.

18. The heart valve of claim 12, wherein the commissures of the first wireform are shorter in height than the commissures of the second wireform.

19. The heart valve of claim 12, wherein the first wireform defines a radius at the commissures, and a length of each leaflet free edge is equal to at least about $2\pi R/3$.

20. The heart valve of claim 1, wherein the wireform is a homogenous preformed wire with either no joints or a crimp joining two free ends thereof.

21. The heart valve of claim 20, wherein the wireform has a cross-section selected from the group consisting of round, oval and square.

* * * * *